United States Patent [19]

Weissmüller et al.

[11] Patent Number: 4,721,786
[45] Date of Patent: Jan. 26, 1988

[54] β-NAPHTHYLALKYLAMINES

[75] Inventors: Joachim Weissmüller, Wuppertal; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 718,128

[22] Filed: Apr. 1, 1985

[30] Foreign Application Priority Data

Apr. 13, 1984 [DE] Fed. Rep. of Germany ....... 3413897

[51] Int. Cl.⁴ .................. C07D 40/06; C07D 251/18; H01N 31/00
[52] U.S. Cl. ........................................ 71/88; 71/94; 71/95; 71/124; 540/484; 540/609; 544/170; 544/174; 544/178; 544/363; 546/205; 546/206; 548/570; 548/578
[58] Field of Search .................. 546/205; 71/124, 88, 71/94, 95; 544/363, 170, , 174, 178; 548/570, 578; 540/609, 484

[56] References Cited

U.S. PATENT DOCUMENTS 4,386,090 5/1983 Moinet et al. ................... 546/205

FOREIGN PATENT DOCUMENTS 7479    2/1980 European Pat. Off. ........... 544/178
3019496 11/1981 Fed. Rep. of Germany ...... 544/178
2371436  6/1978 France ............................. 544/178

Primary Examiner—Richard L. Raymond
Assistant Examiner—Raymond Covington
Attorney, Agent, or Firm—Sprung Horn Kramer & Woods

[57] ABSTRACT

Fungicidally active novel β-naphthylalkylamines of the formula

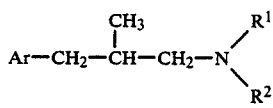

in which
Ar represents optionally substituted β-naphthyl and
$R^1$ and $R^2$, which can be identical or different, represent alkyl or alkenyl or
$R^1$ and $R^2$, together with the nitrogen atom to which they are bonded, represent an optionally substituted saturated heterocyclic radical, which can contain further hetero-atoms,
or plant-tolerated acid addition salts thereof.

6 Claims, No Drawings

β-NAPHTHYLALKYLAMINES

The invention relates to new β-naphthylalkylamines, several processes for their preparation and their use as fungicides.

It is already known that certain arylalkylamino compounds, such as, for example, 1-(4-t-butylphenyl)-1-hydroxy-2-methyl-3-piperidin-1-yl-propane hydrochloride, 1-(4-t-butylphenyl)-1-hydroxy-2-methyl-3-morpholin-4-yl-propane hydrochloride or 1-(4-t-butylphenyl)-1-bromo-2-methyl-3-(2,6-dimethylmorpholin-4-yl)-propane, have fungicidal properties (compare, for example, DE-OS (German Published Specification) No. 3,019,496).

However, the action of these compounds is not always completely satisfactory in all fields of use under certain conditions, especially when low amounts are applied and the concentrations are low.

New β-naphthylalkylamines of the general formula (I)

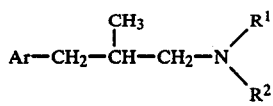

in which
- Ar represents optionally substituted β-naphthyl and
- $R^1$ and $R^2$, which can be identical or different, represent alkyl or alkenyl or
- $R^1$ and $R^2$, together with the nitrogen atom to which they are bonded, represent an optionally substituted saturated heterocyclic radical, which can contain further hetero-atoms, and acid addition salts thereof which are tolerated by plants, have been found.

It has furthermore been found that the new β-naphthylalkylamines of the general formula (I)

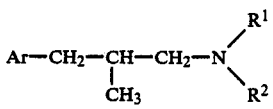

in which
- Ar represents optionally substituted β-naphthyl and
- $R^1$ and $R^2$, which can be identical or different, represent alkyl or alkenyl or
- $R^1$ and $R^2$, together with the nitrogen atom to which they are bonded, represent an optionally substituted saturated heterocyclic radical, which can contain further hetero-atoms, and acid addition salts thereof which are tolerated by plants are obtained by a process in which (a) β-naphthylalkyl compounds of the formula (II)

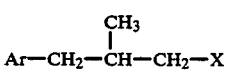

in which
- Ar has the abovementioned meaning and
- X represents an electron-withdrawing leaving group, are reacted with amines of the formula (III)

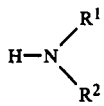

in which
- $R^1$ and $R^2$ have the abovementioned meaning, if appropriate in the presence of a diluent and if appropriate in the presence of an acid-binding agent, or in which (b) the unsaturated aldehydes of the formula (IV)

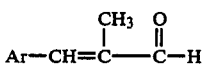

in which
- Ar has the abovementioned meaning, are reacted with amines of the formula (III)

in which
- $R^1$ and $R^2$ have the abovementioned meaning, in the presence of a reducing agent and, if appropriate, in the presence of a catalyst, and, if appropriate, in the presence of a diluent, and, if appropriate, an acid is then added on.

It is also possible to quaternize the β-naphthylalkylamines of the formula (I) according to the invention on the nitrogen by generally customary methods to give the corresponding tetra-substituted ammonium salts.

Finally, it has been found that the new β-naphthylalkylamines of the formula (I) have fungicidal properties.

Surprisingly, the β-naphthylalkylamines of the formula (I) according to the invention exhibit a considerably better fungicidal activity than the arylalkylamino compounds which are known from the prior art, such as, for example, 1-(4-t-butylphenyl)-1-hydroxy-2-methyl-3-piperidin-1-yl-propane hydrochloride, 1-(4-t-butylphenyl)-1-hydroxy-2-methyl-3-morpholin-4-yl-propane hydrochloride, 1-(4-t-butylphenyl)-1-hydroxy-2-methyl-3-(2,6-dimethylmorpholin-4-yl)-propane or 1-(4-t-butylphenyl)-1-bromo-2-methyl-3-(2,6-dimethylmorpholin-4-yl)-propane, which are closely related compounds chemically and from the point of view of their action.

Formula (I) provides a general definition of the β-naphthylalkylamines according to the invention. Preferred compounds of the formula (I) are those
in which
- Ar represents β-naphthyl which is optionally mono-, di- or tri-substituted by identical or different substituents, possible substituents being: halogen, hydroxyl and in each case straight-chain or branched alkyl or alkoxy with in each case 1 to 6 carbon atoms, and
- $R^1$ and $R^2$, which can be identical or different, represent in each case straight-chain or branched alkyl or alkenyl with in each case up to 6 carbon atoms, or
- $R^1$ and $R^2$, together with the nitrogen atom to which they are bonded, represent a saturated 5-membered to 7-membered heterocyclic radical which can contain 1 or 2 further hetero-atoms, in particular nitrogen or oxygen, and is optionally mono-, di- or tri-substituted by identical or different substituents, possible substituents being: in each case straight-chain or branched alkyl or hydroxyalkyl with in each case 1 to 4 carbon atoms.

Particularly preferred β-naphthylalkylamines of the formula (I) are those in which Ar represents β-naphthyl which is optionally mono-substituted or disubstituted by identical or different substituents, possible substituents being: fluorine, chlorine, bromine, hydroxy, methyl, ethyl, n- or i-propyl, n-, i-, s- or t-butyl, methoxy, ethoxy, n- or i-propoxy and $R^1$ and $R^2$, which can be identical or different, represent methyl, ethyl, n- or i-propyl, allyl, butenyl, dimethylallyl or n- or i-pentenyl, or $R^1$ and $R^2$, together with the nitrogen atom to which they are bonded, represent a heterocyclic radical of the formula

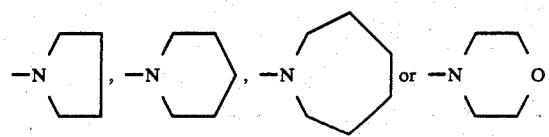

which is optionally mono-, di- or tri-substituted by identical or different substituents, possible substituents being: methyl, ethyl and hydroxymethyl.

The following β-naphthylalkylamines of the formula (I) may be mentioned specifically, in addition to the compounds mentioned in the Preparation Examples:

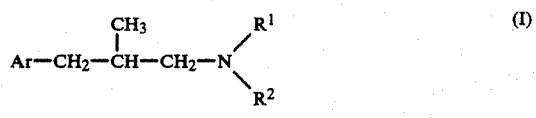

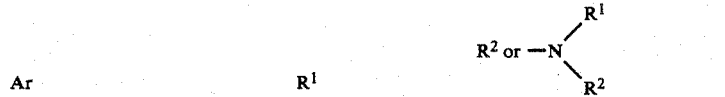

| Ar | $R^1$ | $R^2$ or 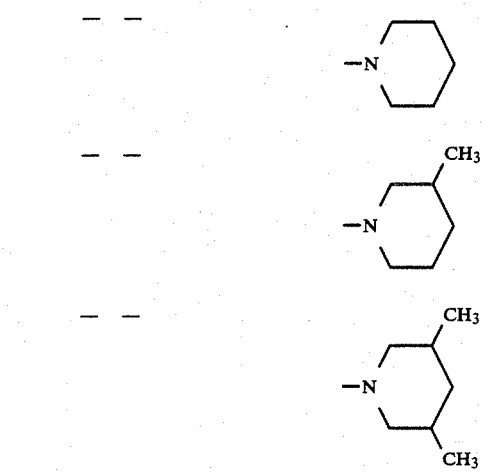 |
|---|---|---|
|  | CH₃ | —CH₂—CH=CH₂ |
| 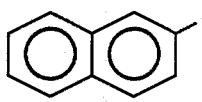 | — | — |
| 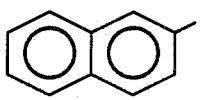 | — | — |
|  | — | — |
| 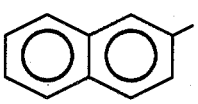 | CH₃ | 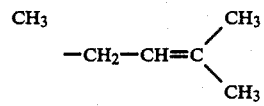 |
| 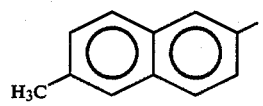 | — | — 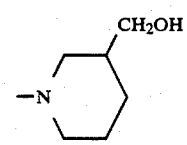 |

-continued $$Ar-CH_2-\underset{\underset{}{\overset{CH_3}{|}}}{CH}-CH_2-N\overset{R^1}{\underset{R^2}{<}} \quad (I)$$

| Ar | R¹ | R² or $-N\overset{R^1}{\underset{R^2}{<}}$ |
|---|---|---|
| 6-methyl-1-chloro-2-methoxynaphthalene | — | 2,6-dimethylmorpholino |
| 6-methyl-1-chloro-2-methylnaphthalene | — | 3-methylpiperidino |
| 1,4-dimethoxy-3-methylnaphthalene | CH₃ | $-CH_2-CH=C\overset{CH_3}{\underset{CH_3}{<}}$ |
| 6-methyl-1-chloro-2-hydroxynaphthalene | — | 3,5-dimethylpiperidino |
| 6-methyl-1,2-dichloronaphthalene | — | morpholino |
| 1-chloro-2-methylnaphthalene | CH₃ | $-CH_2-CH=CH_2$ |
| 1-methyl-2-naphthyl | — | 3-(hydroxymethyl)piperidino |
| 6-chloro-2-naphthyl | — | 3-methylpiperidino |

-continued

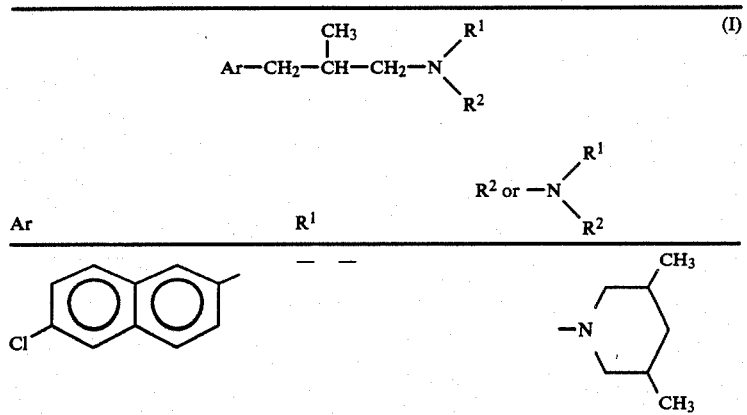

If, for example, 1-methanesulphonyloxy-2-methyl-3-β-naphthyl-propane and 2,6-dimethylmorpholine are used as starting substances, the course of the reaction in process (a) according to the invention can be represented by the following equation:

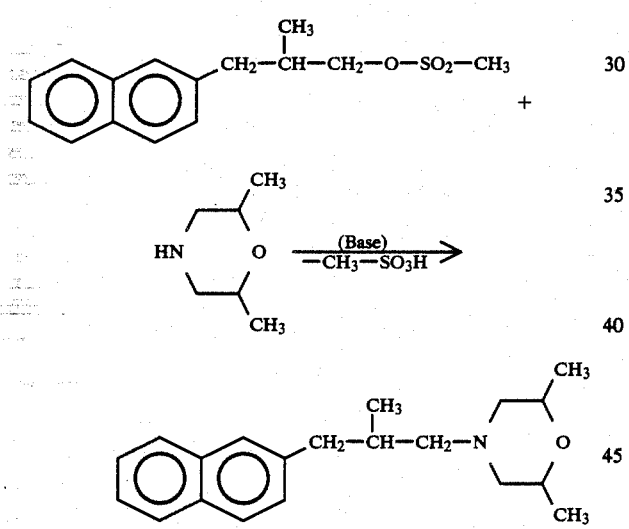

If, for example, 2-methyl-3-β-naphthyl-acrolein and 3,5-dimethyl-piperidine are used as starting substances and hydrogen is used as the reducing agent, the course of the reaction in process (b) according to the invention can be represented by the following equation:

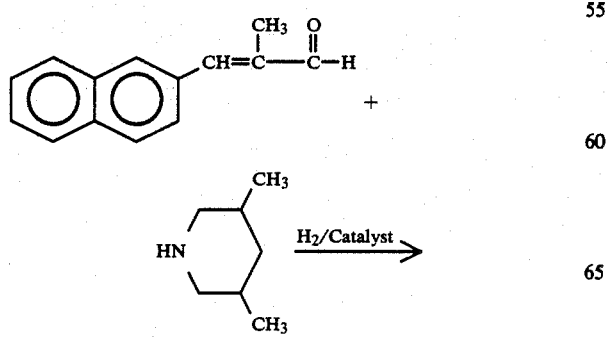

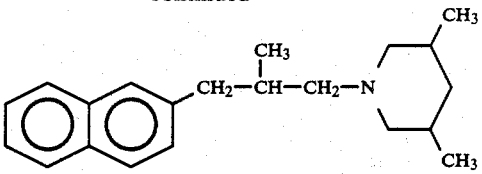

Formula (II) provides a general definition of the β-naphthylalkyl compounds required as starting substances for carrying out process (a) according to the invention. In this formula (II), Ar preferably represents those optionally substituted β-naphthyl radicals which have already been mentioned as preferred for this radical in the description of the substances of the formula (I) according to the invention. X preferably represents halogen, in particular chlorine, bromine or iodine, or in each case optionally substituted alkyl- or aryl-sulphonyloxy, in particular methanesulphonyloxy, trifluoromethanesulphonyloxy or p-toluenesulphonyloxy.

The β-naphthylalkyl compounds of the formula (II) are not yet known.

They are obtained by a process in which 2-methyl-3-β-naphthyl-acrylic acid esters of the formula (V)

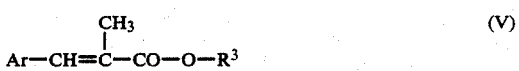

in which
    Ar has the abovementioned meaning and
    $R^3$ represents alkyl, in particular methyl or ethyl,
are initially reduced, in a first stage, with a reducing agent, such as, for example, lithium aluminum hydride, if appropriate in the presence of a diluent, such as, for example, diethyl ether, at temperatures between −20° C. and +60° C., and the alcohols thus obtained, of the formula (VI)

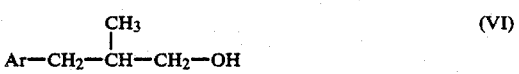

in which
    Ar has the abovementioned meaning, are reacted to form derivatives by generally customary processes, thus, for example, are either sulphonated with sulphonic acid halides of the formula (VII)

$$R^4-SO_2-Hal \quad (VII)$$

in which
R[4] represents in each case optionally substituted alkyl or aryl, in particular methyl, trifluoromethyl or p-tolyl, and Hal represents halogen, in particular chlorine or bromine, if appropriate in the presence of a diluent, such as, for example, methylene chloride, and if appropriate in the presence of an acid-binding agent such as, for example, triethylamine, at temperatures between −20° C. and +120° C., or are halogenated with halogenating agent, such as thionyl chloride, phosphorus pentachloride, phosphorus tribromide, hydrobromic acid or hydriodic acid, if appropriate in the presence of a diluent, such as, for example, carbon tetrachloride, and if appropriate in the presence of a catalyst, such as, for example, pyridine, at temperatures between +20° C. and +180° C.

The 2-methyl-3-β-naphthylacrylic acid esters of the formula (V) are known (compare, for example, Indian J. Chem. Section B, 22B (4), 352–354 [1983] or J. org. Chemistry 33, 4351–4362 [1968]), or they can be prepared in a simple manner analogous to processes which are known in principle (compare, for example, J. Chem. Soc. 1961, 3160). The sulphonic acid halides of the formula (VII) are generally known compounds of organic chemistry.

Formula (IV) provides a general definition of the unsaturated aldehydes required as starting substances for carrying out process (b) according to the invention. In this formula (IV), Ar preferably represents those optionally substituted β-naphthyl radicals which have already been mentioned as preferred for this radical in the description of the substances of the formula (I) according to the invention.

The unsaturated aldehydes of the formula (IV) are not yet known. They are obtained, however, by processes which are known in principle, in which β-naphthaldehydes of the formula (VIII)

$$\overset{O}{\underset{}{\text{Ar}-\overset{\|}{C}-H}} \quad (VIII)$$

in which
Ar has the abovementioned meaning, are reacted with propionaldehyde of the formula (IX)

$$\overset{O}{\underset{}{C_2H_5-\overset{\|}{C}-H}} \quad (IX)$$

if appropriate in the presence of a diluent, such as, for example, methanol, and if appropriate in the presence of a catalyst, such as, for example, sodium hydroxide, at temperatures between −20° C. and +120° C., and water is split off from the addition products thus obtainable, of the formula (X)

$$\text{Ar}-\overset{OH}{\underset{}{CH}}-\overset{CH_3}{\underset{}{CH}}-\overset{O}{\underset{}{\overset{\|}{C}}}-H \quad (X)$$

in which
Ar has the abovementioned meaning,
likewise in a generally customary manner, with an acid catalyst, such as, for example, acetic acid, if appropriate in the presence of a diluent, such as, for example, methanol, at temperatures between +20° C. and 180° C.

The β-naphthaldehydes of the formula (VIII) and propionaldehyde of the formula (IX) are generally known compounds of organic chemistry.

Formula (III) provides a general definition of the amines furthermore required as starting substances for carrying out processes (a) and (b) according to the invention. In this formula (III), R[1] and R[2] preferably represent those radicals which have already been mentioned as preferred for these substituents in the description of the substances of the formula (I) according to the invention.

The amines of the formula (III) are likewise generally known compounds of organic chemistry.

Possible diluents for carrying out process (a) according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide. However, the reaction can also be carried out without diluents.

If appropriate, process (a) according to the invention can be carried out in the presence of an acid-binding agent.

Possible acid-binding agents are all the usual inorganic or organic bases. These include, for example, alkali metal hydroxides, such as sodium hydroxide or potassium hydroxide; alkali metal carbonates, such as sodium carbonate, and tertiary amines, such as triethylamine, N,N-dimethylaniline, pyridine, N,N-dimethylaminopyridine, diazabicyclooctane (DABCO), diazabicyclonone (DBN) or diazabicycloundecene (DBU).

An appropriate excess of amine of the formula (III) used as the reactant can simultaneously serve as the acid-binding agent and, if the amine is in liquid form, also as the diluent.

The reaction temperatures can be varied within a substantial range in carrying out process (a) according to the invention. In general, the reaction is carried out at temperatures between 0° C. and 250° C., preferably at temperatures between 30° C. and 180° C.

For carrying out process (a) according to the invention, in general 1.0 to 10.0 moles, preferably 1.0 to 5.0 moles, of amine of the formula (III) and, if appropriate, 1.0 to 10.0 moles, preferably 1.0 to 5.0 moles, of acid-binding agent are employed per mole of β-naphthylalkyl compound of the formula (II). For working up, the reaction product is separated off from water-soluble impurities by partition in an aqueous-organic two-phase system, and is isolated in the generally customary manner and then, if appropriate, purified by column chromatography.

Possible diluents for carrying out process (b) according to the invention are likewise inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, or alcohols, such as methanol, ethanol or isopropanol. However, the reaction can also be carried out without diluents.

Possible reducing agents are all the usual compounds which reduce carbonyl groups. Molecular hydrogen of formic acid is preferably used.

Possible catalysts are likewise all the usual hydrogenation catalysts. Noble metal, noble metal oxide or noble metal hydroxide catalysts or so-called Raney catalysts, in particular platinum, platinum oxide and Raney nickel, are preferably used.

The reaction temperatures can be varied within a substantial range in carrying out process (b) according to the invention. In general, the reaction is carried out at temperatures between 0° C. and +250° C., preferably at temperatures between +20° C. and +200° C.

Process (b) according to the invention can be carried out under normal pressure or under increased pressure. In general, it is carried out under between 1 atmosphere and 300 atmospheres, preferably between 1 atmosphere and 200 atmospheres.

For carrying out process (b) according to the invention, in general 1.0 to 5.0 moles, preferably 1.0 to 2.0 moles, of amine of the formula (III) and 1.0 to 10 moles, preferably 1.0 to 5.0 moles, of reducing agent and, if appropriate, 0.01 to 0.1 mole of catalyst are employed per mole of unsaturated aldehyde of the formula (IV). The compounds of the formula (I) are worked up and isolated in the generally customary manner.

If appropriate, the compounds of the formula (I) according to the invention can then be converted into acid addition salts.

The following acids can preferably be used for the preparation of physiologically acceptable acid addition salts of the compounds of the formula (I): the hydrogen halide acids, such as, for example, hydrochloric acid and hydrobromic acid, in particular hydrochloric acid, and furthermore phosphoric acid, nitric acid, sulphuric acid, monofunctional, bifunctional and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

The active compounds according to the invention exhibit a powerful microbicidal action and can be employed in practice for combating undesired microorganisms. The active compounds are suitable for use as plant protection agents.

Thus, for example, fungicidal agents are employed in plant protection for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compounds according to the invention can be used with particularly good success for combating cereal diseases, such as, for example, against the leaf spot of wheat causative organism (*Leptosphaeria nodorum*), against the stripe disease of barley causative organism (*Drechslera graminea*), against the net blotch disease of barley causative organism (*Pyrenophora teres*) and against the powdery mildew of cereal causative organism (*Erysiphe graminis*), for combating rice diseases, such as, for example, against the rice spot disease causative organism (*Pyricularia oryzae*), or for combating vegetable diseases, such as, for example, against the powdery mildew of cucumber causative organism (*Sphaerotheca fuliginea*). Besides an outstanding protective activity, the active compounds according to the invention also exhibit extremely good systemic properties.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperatures and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and as mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, brushing on and the like. It is furthermore possible to apply the active compounds by the ultralow volume method or to inject the active compound formulation or the active compound itself into the soil. The seeds of the plants can also be treated.

In the treatment of parts of plants, the active compound concentrations in the use forms can be varied within a substantial range. They are in general between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.2%, are required at the place of action.

PREPARATION EXAMPLES

Example 1

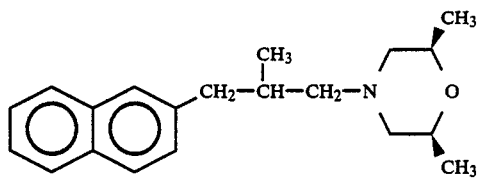

10.8 g (0.04 mole) of 1-methanesulphonyl-2-methyl-3-β-naphthyl-propane and 9 g (0.078 mole) of cis-2,6-dimethylmorpholine are stirred at a bath temperature of 140° C. for 15 hours. Water is added to the resulting reaction mixture and the mixture is extracted several times with ether. The combined organic phases are dried over sodium sulphate and freed from the solvent in vacuo; the oily residue is purified by column chromatography (silica gel 60/petroleum ether-ether 2:1). 6.2 g (52% of theory) of cis-1-(2,6-dimethylmorpholin-4-yl)-2-methyl-3-β-naphthyl-propane of refractive index $n_D^{20}$: 1.5527 are obtained.

Preparation of the starting compound

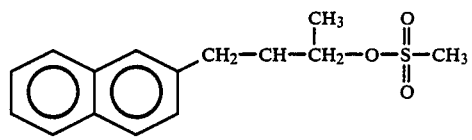

11 g (0.1 mole) of methanesulphonyl chloride are added dropwise to 14 g (0.074 mole) of 2-methyl-3-β-naphthyl-propanol (crude) in 80 ml of absolute pyridine at 0° C., with stirring, the mixture is stirred for a further 16 hours at room temperature when the addition has ended, excess pyridine is removed by distillation in vacuo, the residue is taken up in water, the mixture is extracted several times with methylene chloride, the extract is dried over sodium sulphate and the solvent is removed in vacuo. 13.6 g (66% of theory) of 1-methanesulphonyloxy-2-methyl-3-β-naphthyl-propane are obtained as an oil. (IR: $\gamma = 1345$ and $1180 \text{ cm}^{-1}$).

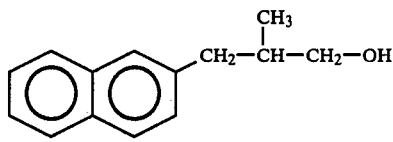

12 g (0.05 mole) of ethyl 2-methyl-3-β-naphthylacrylate are added dropwise to a suspension of 1.9 g (0.05 mole) of lithium aluminum hydride in 150 ml of absolute ether in a dry nitrogen atmosphere, while cooling with ice. When the addition has ended, the mixture is warmed at the reflux temperature for 8 hours and, after the reaction mixture has been cooled, 15 ml of 5 percent strength sulphuric acid are then slowly added dropwise, with cooling, the solid which has precipitated is filtered off with suction, the filtrate is dried over sodium sulphate, the solvent is removed in vacuo and the residue is recrystallized from ether/petroleum ether. 7.1 g of 2-methyl-3-β-naphthyl-propanol of melting point 71°–74° C. which, according to the gas chromatogram, is contaminated with 2-methyl-1-β-naphthyl-propen-3-ol and can be used in the next reaction stage without further purification, are obtained.

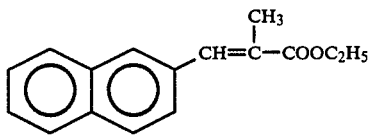

40 g (0.2 mole) of ethyl β-ethoxalylpropionate are added to a suspension of 5.5 g (0.2 mole) of 80% pure sodium hydride in 300 ml of absolute xylene at 70° C. When the evolution of hydrogen has ended, 31.2 g (0.2 mole) of β-naphthaldehyde, dissolved in xylene, are added dropwise and, when the addition has ended, the mixture is heated at the boiling point for 90 minutes.

150 ml of water are added to the cooled reaction mixture, and the organic phase is separated off, washed with 7% strength sodium carbonate solution, dried over sodium sulphate and concentrated. The residue is distilled in vacuo. 21.7 g (45.2% of theory) of ethyl 2-methyl-3-β-naphthyl-acrylate of boiling point 110° C./0.13 mbar are obtained.

Example 2

Analogously to Example 1 there can be prepared the compound

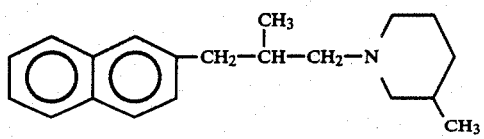

with the refractive index $n_D^{20}$: 1.5547.

USE EXAMPLES

The compounds shown below are employed as comparison substances in the use examples which follow:

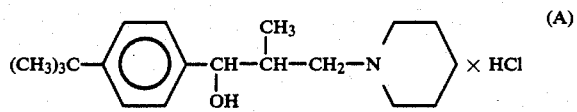

(A)

1-(4-t-Butylphenyl)-1-hydroxy-2-methyl-3-piperidin-1-yl-propane hydrochloride

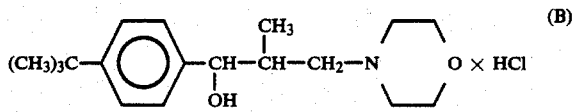

(B)

1-(4-t-Butylphenyl)-1-hydroxy-2-methyl-3-morpholin-4-yl-propane hydrochloride

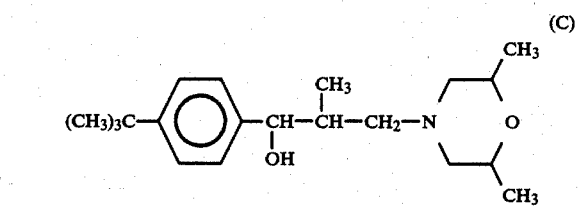

(C)

1-(4-t-Butylphenyl)-1-hydroxy-2-methyl-3-(2,5-dimethylmorpholin-4-yl)-propane

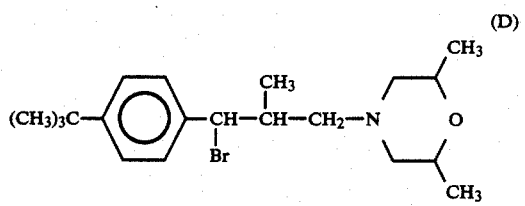

(D)

1-Bromo-1-(4-t-butylphenyl)-2-methyl-3-(2,6-dimethylmorpholin-4-yl)-propane (all known from DE-OS (German Published Specification) No. 3,019,496)

Example A

*Leptosphaeria nodorum* test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain in an incubation cabinet at 20° C. and 100% relative atmospheric humidity for 48 hours.

The plants are placed in a greenhouse at a temperature of about 15° C. and a relative atmospheric humidity of about 80%.

Evaluation is carried out 10 days after the inoculation.

In this test, a clearly superior activity compared with the prior art is shown, for example, by the compound according to preparation Example 1.

Example B

*Pyrenophora teres* test (barely)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Pyrenophora teres*. The plants remain in an incubation cabinet at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compound according to preparation Example 1.

Example C

*Drechslera graminea* test (barley)/seed treatment (syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

In this test, a clearly superior activity compared with the prior art is shown, for example, by the compound according to preparation Example 1.

Example D

Sphaerotheca test (cucumber)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compound according to preparation Example 1.

Example E

Pyricularia test (rice)/systemic

Solvent: 12.5 parts by weight of acetone
Emulsifier: 0.3 parts by weight of alkylaryl polyglycol ether.

To produce a suitable preparation of active compound, 1 part by weight of active compound is mixed with the stated amounts of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compound according to preparation Example 1.

It will be understood that the specification and examples are illustrative but not limitative of the present invention and that other embodiments within the spirit and scope of the invention will suggest themselves to those skilled in the art.

We claim:

1. A β-naphthylalkylamine of the formula

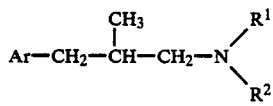

in which
Ar represents β-naphthyl which is optionally mono-, di- or tri-substituted by identical or different substituents from the group comprising halogen and alkyl and alkoxy with in each case 1 to 6 carbon atoms, and
$R^1$ and $R^2$, together with the nitrogen atom to which they are bonded, represent a heterocyclic radical of the formula

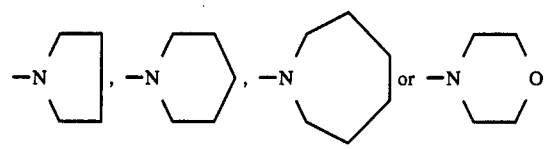

which is optionally mono-, di- or tri-substituted by identical or different substituents from the group comprising in each case straight-chain or branched alkyl and hydroxyalkyl with in each case 1 to 4 carbon atoms,
or a plant-tolerated acid addition salt thereof.

2. A β-naphthylalkylamine or salt according to claim 1, in which
Ar represents β-naphthyl which is optionally mono-substituted or disubstituted by identical or different substituents from the group comprising fluorine, chlorine, bromine, hydroxy, methyl, ethyl, n- or i-propyl, n-, i-, s- or t.-butyl, methoxy, ethoxy and n- or i-propoxy, and
$R^1$ and $R^2$, which can be identical or different, represent methyl, ethyl, n- or i-propyl, allyl, dimethylallyl, butenyl or n- or i-pentenyl, or
$R^1$ and $R^2$, together with the nitrogen atom to which they are bonded, represent a heterocyclic radical of the formula

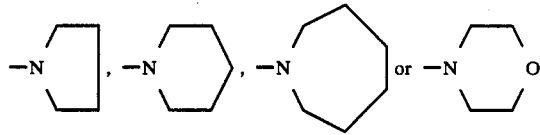

which is optionally mono-, di- or tri-substituted by identical or different substituents from the group comprising methyl, ethyl and hydroxymethyl.

3. A compound according to claim 1, wherein such compound is 1-(2,6-dimethylmorpholin-4-yl)-2-methyl-3-β-naphthyl-propane of the formula

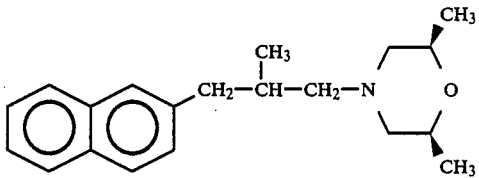

or a plant-tolerated acid addition salt thereof.

4. A compound according to claim 1, wherein such compound is 2-methyl-1-(3-methyl-piperidin-1-yl)-3-β-naphthyl-propane of the formula

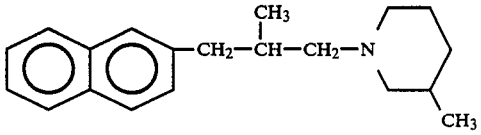

or a plant-tolerated acid addition salt thereof.

5. A fungicidal composition comprising a fungicidally effective amount of a compound or salt according to claim 1 in admixture with a diluent.

6. A β-naphthylalkylamine or salt according to claim 2,
in which
Ar represents β-naphthyl which is optionally mono-substituted or di-substituted by methyl, ethyl, n- or i-propyl or n-, i-, s- or ti-butyl, $R^1$ and $R^2$ together with the nitrogen atom to which they are bonded, represent a heterocyclic radical of the formula

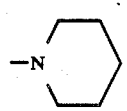

which is optionally mono-, di- or tri-substituted by identical or different substituents from the group comprising methyl, ethyl and hydroxymethyl.

* * * * *